(12) United States Patent
Patel et al.

(10) Patent No.: US 7,118,574 B2
(45) Date of Patent: Oct. 10, 2006

(54) ARTHROSCOPIC BONE BURR DEVICE

(75) Inventors: Samit J. Patel, Maple Shade, NJ (US); Thomas Ryan, Flemington, NJ (US); Simon Cohn, North Arlington, NJ (US); Martin Nohilly, Hoboken, NJ (US); Julian Mark Ebbutt, Marshfield (GB); Alistair Fleming, Canton (GB)

(73) Assignee: Ethicon, Inc, Somerville, NJ (US)

( * ) Notice: Subject to any disclaimer, the term of this patent is extended or adjusted under 35 U.S.C. 154(b) by 690 days.

(21) Appl. No.: 10/172,738

(22) Filed: Jun. 14, 2002

(65) Prior Publication Data

US 2003/0233111 A1    Dec. 18, 2003

(51) Int. Cl.
*A61B 17/16*    (2006.01)

(52) U.S. Cl. .......................................................... 606/80

(58) Field of Classification Search .................. 606/79, 606/80, 159, 167, 170, 180
See application file for complete search history.

(56) References Cited

U.S. PATENT DOCUMENTS

| 4,842,578 A | 6/1989 | Johnson et al. |
| 6,126,667 A * | 10/2000 | Barry et al. ................ 606/159 |

* cited by examiner

*Primary Examiner*—Eduardo C. Robert
*Assistant Examiner*—Jessica R. Baxter (57) ABSTRACT

An arthroscopic bone burr having an articulated sheath tube. The sheath tube may be articulated angularly and transversely relative to the housing by a ball-type joint, a flange-in-socket joint with sufficient play to permit displacement of the sheath tube, or by use of an elastomer. Anti-rotation means are provided to prevent the sheath tube from rotating relative to the housing.

20 Claims, 11 Drawing Sheets

ARTHROSCOPIC BONE BURR DEVICE

FIELD OF THE INVENTION

The present invention relates to surgical instruments, and more particularly to powered rotating surgical tools having a cutting element or burr proximate a tip thereof for removing tissue such as cartilage or bone from a surface against which it is applied.

BACKGROUND OF THE INVENTION

Known arthroscopic bone burr instruments utilize a rotating inner tube/shaft to which the burr (cutting) element is attached and a rigid, stationary, outer tube to cover the rotating inner tube. The distal end of the outer tube has an opening through which the burr element may contact the tissue to be acted upon. When the burr element is pressed against a tissue surface, e.g., to abrade away a portion of the surface of a bone, it typically experiences loading in a direction perpendicular to the axis of rotation (side loading). Known designs may utilize the outer tube to support the burr element and rotating inner tube against side loading. A bearing formed from a material having a lower coefficient of friction may be incorporated between the inner rotating tube and the stationary, rigid outer tube proximate the burr element to reduce the friction resulting from the rotating inner tube bearing against the stationary outer tube. Notwithstanding a reduction of friction by use of a bearing, side loading experienced during arthroscopic surgery may result in wear of the rotating inner tube and/or the bearing and/or the stationary outer tube. There is a need in this art for novel, improved bone burrs for use in arthroscopic surgical procedures, which overcome the deficiencies of the bone burrs of the prior art.

SUMMARY OF THE INVENTION

The problems and disadvantages associated with conventional arthroscopic bone burr instruments are overcome by the present invention which includes a surgical tool for removing material from a surface and having a front tool assembly coupled to a handle. The front tool assembly has a housing and a rotatable burr shaft extending therefrom with a burr attached at one end of the burr shaft and a rotary drive apparatus coupled to the other end for selectively rotating the burr shaft as controlled by a user. A sheath tube is disposed substantially coaxially over the burr shaft and is attached at a first end to the front tool assembly housing. The sheath tube has an opening proximate a second end thereof through which the burr contacts the surface for removing material. The sheath tube is attached to the front tool assembly housing at an articulation, with the articulation enabling the sheath tube to be displaced from axial alignment with the front tool assembly housing.

These and other aspects and advantages of the present invention will become more apparent from the following description and accompanying drawings.

BRIEF DESCRIPTION OF THE FIGURES

For a better understanding of the present invention, reference is made to the following detailed description of several exemplary embodiments considered in conjunction with the accompanying drawings, in which.

DETAILED DESCRIPTION OF THE FIGURES

Figure 1:
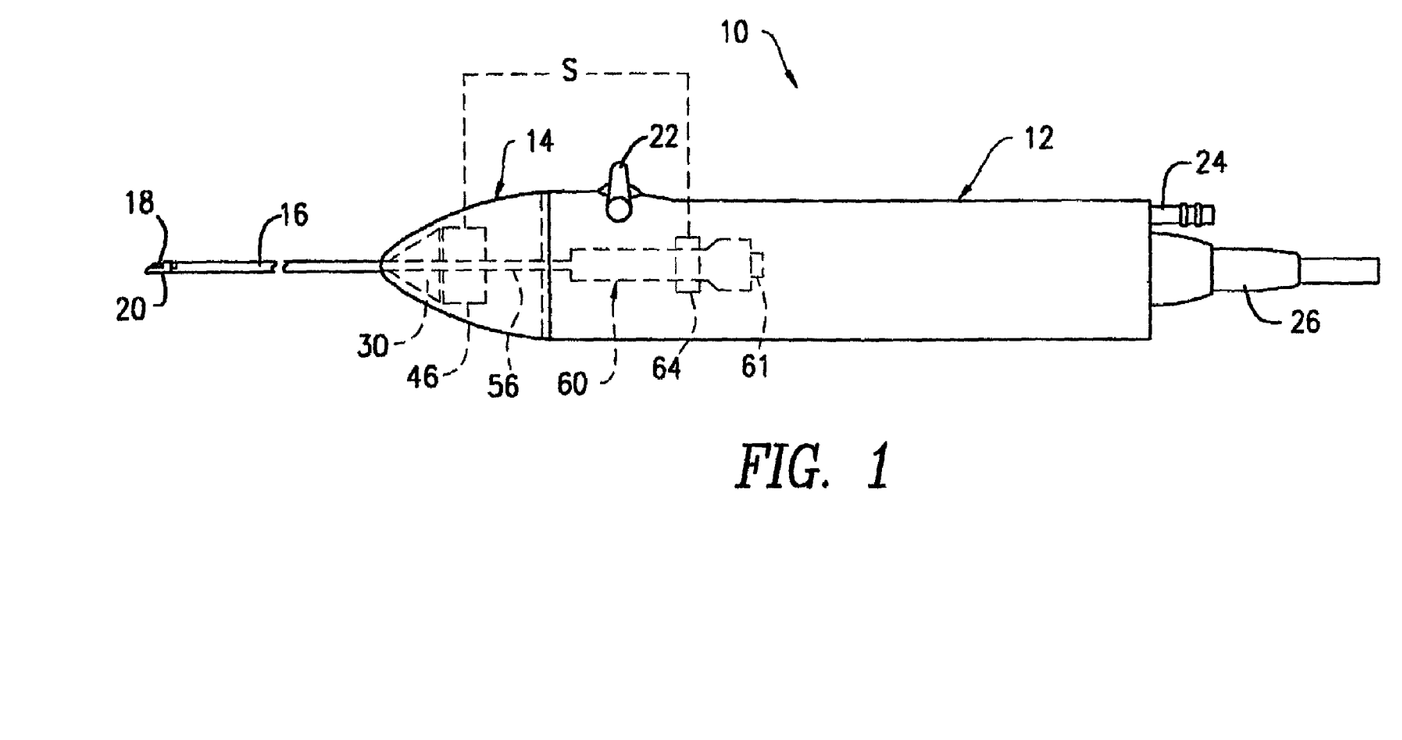
FIG. 1 is a side view of an arthroscopic bone burr device in accordance with a first embodiment of the present invention with selected internal components shown diagrammatically.

FIG. 1 shows an arthroscopic bone burr device 10 suitable for use in arthroscopic surgery, for example to remove a surface layer of bone tissue to induce blood flow and subsequent reestablishment of articular cartilage. The device 10 has a handle portion 12 which is used to hold the device 10 and for containing an electric motor for powering the device 10. Other types of drive mechanisms are known such as hydraulic, vacuum and gas driven motors, as well as a remotely driven cable. A front tool assembly 14 attaches at one end of the handle 12. A sheath tube 16 extends in a distal direction from the front tool assembly 14 with a burr 18 and a burr shield 20 disposed at the distal end of the sheath tube 16. As is known, the burr 18 is typically a hardened steel tool with a plurality of cutters on the surface thereof, such that when the burr 18 is rotated at high speed, it will cut into a surface against which is pressed. The burr shield 20 is utilized to limit the exposure of surrounding tissue to the burr 18 such that the burr 18 can be directed against a single surface without inadvertently injuring surrounding tissue which is protected by the burr shield 20. The arthroscopic bone burr device 10 has a control lever 22 for controlling the direction and speed of rotation of the burr 18. A suction nipple 24 extends from the rear of the handle 12 in a conventional manner and is utilized to draw fluid from the surgical site through the front tool assembly 14 and through the handle 12 to clear debris generated by the operation of the burr 18. More particularly, insufflation fluids are pumped to the surgical site and drawn through the arthroscopic bone burr device 10 along with the debris generated by operation of the device 10, thereby keeping the site clear for visualization and removing contaminants from the surgical site, for example a knee joint. A power supply 26 extends from the rear of the handle 12, such as an electrical supply cord, a pressurized gas hose or remotely driven cable, as known in the art. The elements shown in dotted lines, e.g., burr shaft 56, will be described below in reference to FIGS. 2–6C, after which description, their depiction in FIG. 1 will be described.

Figure 3:
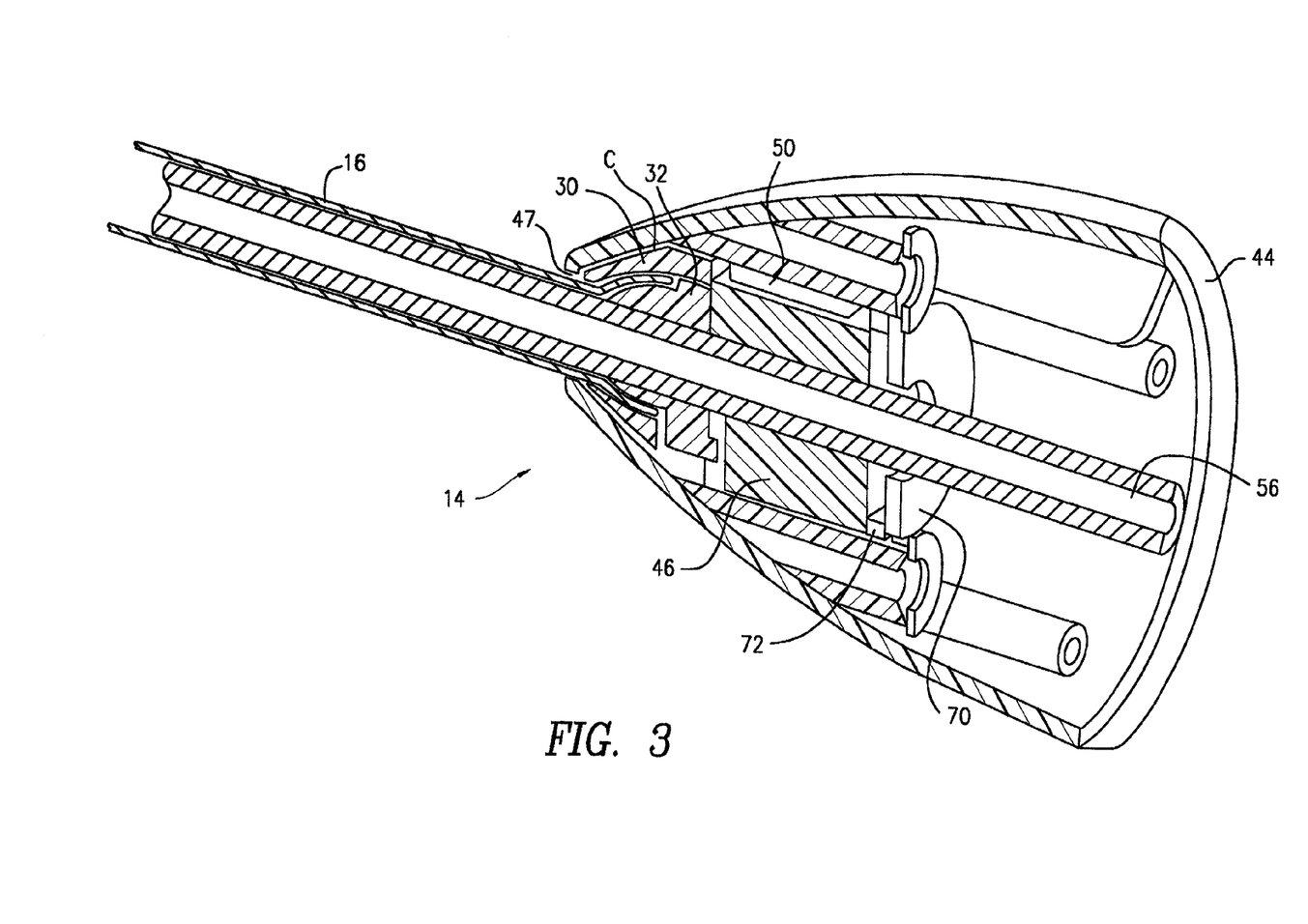
FIG. 3 is a cross-sectional view of the assembly of FIG. 2 in an assembled state taken along section line III—III and looking in the direction of the arrows.
Figure 4:
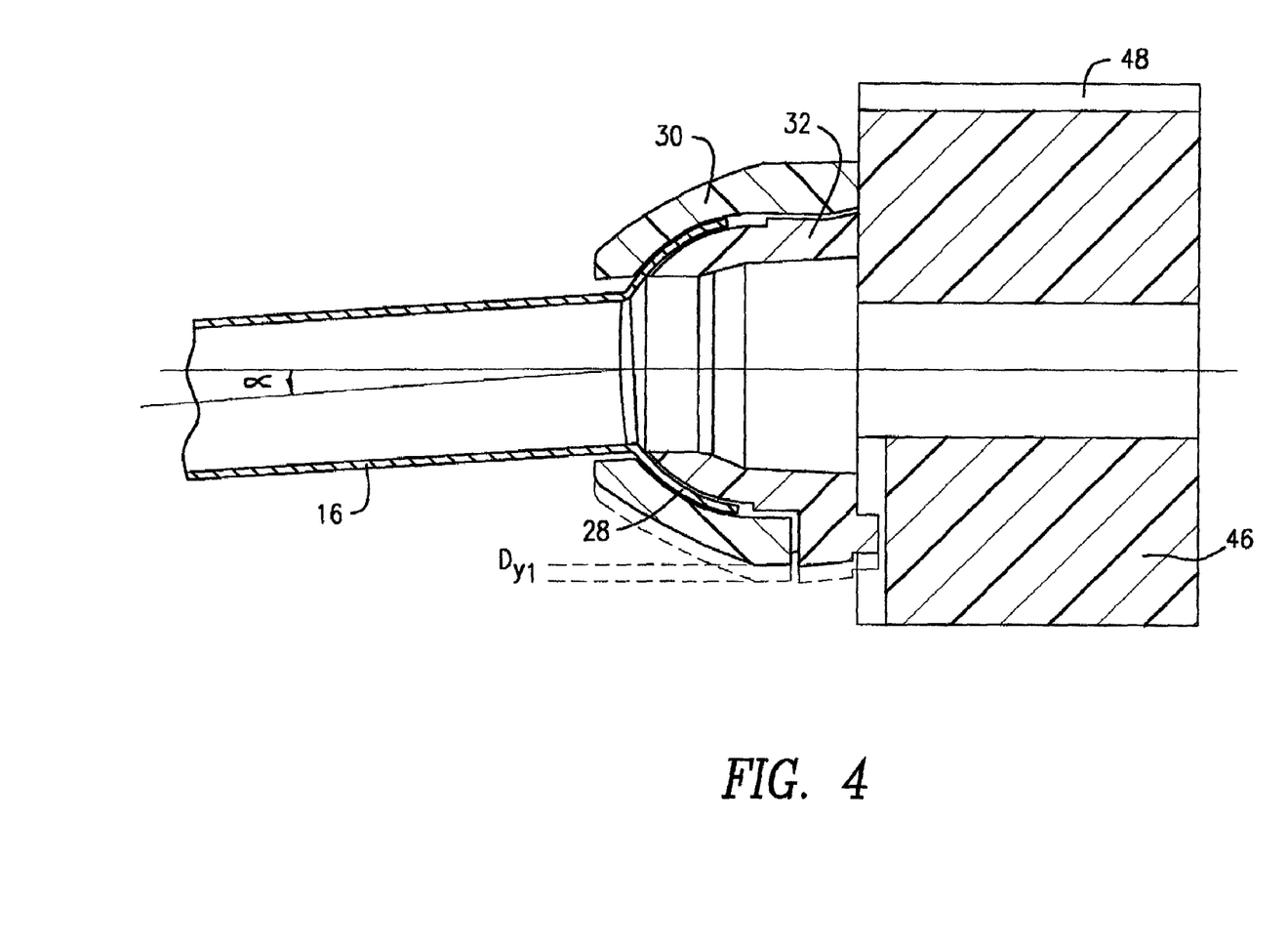
FIG. 4 is an enlarged cross-sectional view of a sheath tube, associated support and bearing shown in FIG. 3 with the burr shaft removed and the sheath tube hanging limp.
Figure 5:
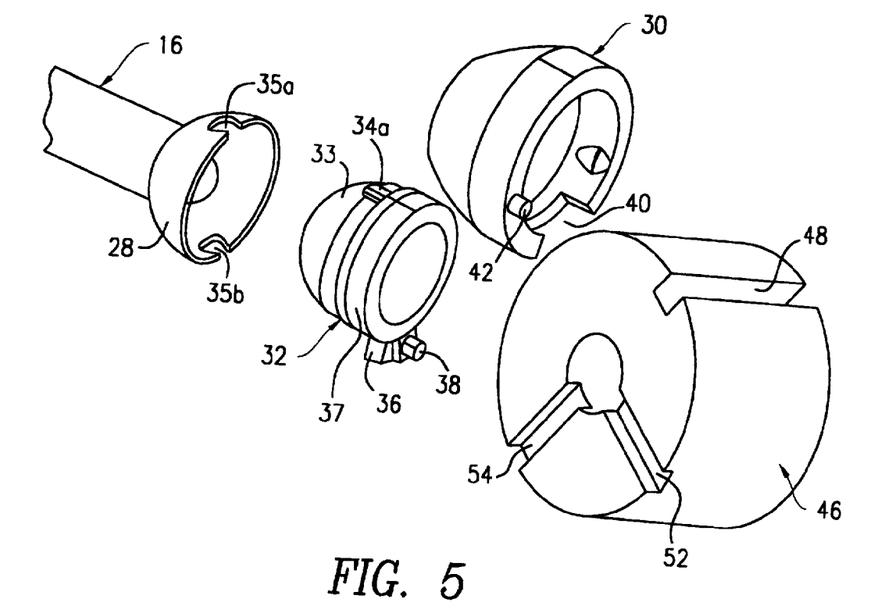
FIG. 5 is an exploded view of the sheath tube, support and bearing shown in FIG. 4.
Figure 6A:
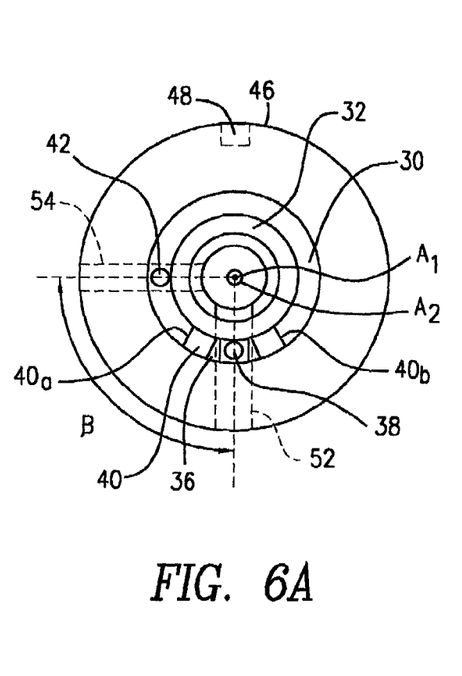
FIGS. 6A–6C are diagrammatic views of the elements of FIG. 5 in three different positions.
Figure 6B:
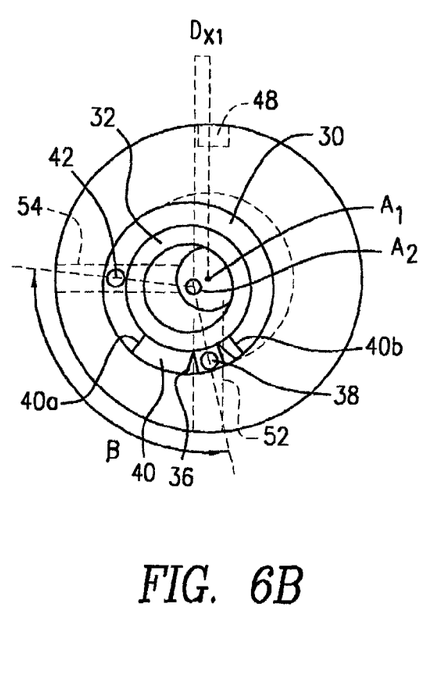
Figure 6C:
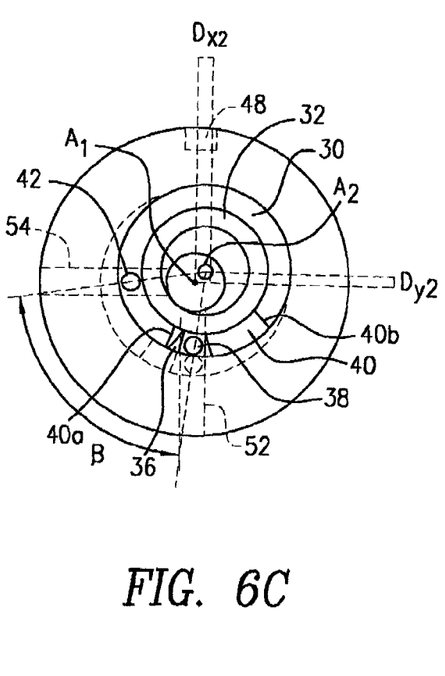

FIGS. 2–6C show additional details of the present invention. More particularly, the sheath tube 16 is shown as having a ball flange 28 at the proximal end thereof. The ball flange 28 is captured between a socket element 30 and a ball element 32. As shown in FIG. 5, the ball element 32 has a ball portion 33, a pair of alignment ribs 34a, 34b (not visible) and a cylindrical portion 37. When the ball portion 33 is inserted into the ball flange 28, the alignment ribs 34a, 34b are received in corresponding anti-rotation notches 35a and 35b. The anti-rotation notches 35a, 35b have a longer extension than the alignment ribs 34a, 34b and flare outwardly in a distal direction, such that the sheath tube 16 may be pivoted omni-directionally about the alignment ribs 34a, 34b over a selected range of motion while maintaining contact between the ball portion 33 and the ball flange 28 in ball and socket fashion. The sheath tube 16 is inserted through the socket element 30 such that the socket element 30 covers the distal face of the ball flange 28 and when juxtaposed against the ball element 32, the ball flange 28 is captured between the socket element 30 and the ball element 32. The ball element 32 has a tab 36 extending from a proximal edge thereof, which such tab 36 has a locator pin 38 extending therefrom in a proximal direction. The tab 36 is received in a notch 40 provided in a proximal edge of the socket element 30 and the socket element 30 has a locator pin 42 extending from a proximal edge such that when the socket element 30 and the ball element 32 are assembled together with the ball flange 28 captured therebetween, the locator pin 38 and locator pin 42 are disposed at approximately 90° relative to one another. As shown in FIGS. 6A–6C, which are described more fully below, the relative angular position of locator pins 38 and 40 is variable due to the rotational play of tab 36 in notch 40, which such arrangement permits translational movement of sheath tube 16 relative to housing 44.

Referring to FIGS. 3–5, the sheath tube 16 with associated socket element 30 and ball element 32 are received in housing 44 of the front tool assembly 14. A clearance C is provided between socket element 30 and housing 44 to allow relative translational motion, i.e., socket element 30 is not coaxially fixed relative to housing 44. A bearing 46 inserts within the housing 44 behind the ball element 32, with the sheath tube 16 extending through opening 47 in housing 44. A notch 48 provided on an outer peripheral surface of the bearing 46 receives a mating key 50 extending from an interior surface of the housing 44. When the bearing 46 is installed within the housing 44, pin recesses 52 and 54 align with and receive therein locator pins 42 and 38, respectively. The notch 48 and key 50 prevent the bearing 46 from rotating relative to the housing 44 which is preferably rigidly held in coaxial alignment with housing 44. The locator pins 38 and 42, when positioned in the pin recesses 54 and 52, prevent the socket element 30 and the ball element 32 from rotating relative to the bearing 46 and housing 44. The alignment ribs 34a, 34b extending into the anti-rotation notches 35a and 35b prevent the sheath tube 16 from rotating relative to the ball portion 32. As a consequence, sheath tube 16 is rotationally fixed relative to housing 44 while still being able to pivot omni-directionally and move transversely relative to housing 44.

The ball portion 33 of the ball element 32 is preferably in the form of a hemisphere. Ball flange 28 preferably has the same internal spheric radius as that of ball portion 33, but is less than a complete hemisphere, such that the ball flange 28 may be rotated over the surface of the ball portion 33 omni-directionally to a predetermined extent prior to its contacting the cylindrical portion 37 of the ball element 32 which constitutes a travel stop. Alternatively, the ball element 32 may be a greater spheric segment than a hemisphere, with the ball flange 28 being hemispheric. As noted above, the notches 35a and 35b preferably have a depth which is greater than the extent of alignment ribs 34a, 34b, such that the freedom of motion of the ball flange 28 over the ball portion 33 is not restricted in the direction parallel to the alignment ribs 34a, 34b. At least one of the alignment ribs 34a, 34b remains engaged with the associated anti-rotation notch 35a, 35b at all times, i.e., even though the sheath tube 16 and ball flange 28 are tipped on the ball portion 33 to the maximum extent of angular displacement. In this manner, the sheath tube 16 has freedom of motion to be oriented at an angular displacement relative to the axis of the housing 44, but the sheath tube 16 may not be rotated relative to the ball element 32 due to the insertion of at least one of the alignment ribs 34a, 34b into the corresponding anti-rotation notches 35a, 35b.

As shown in FIG. 4, the above-described assembly 16, 28, 30, 32 constitutes a ball and socket joint or articulation that allows the sheath tube 16 to be omni-directionally tilted relative to the axis of the bearing 48 and socket and ball elements 30, 32 by an angle $\alpha$, as well as to be moved transversely in a direction perpendicular to the axis of bearing 46, e.g., by displacement $D_{y1}$.

Figure 2:
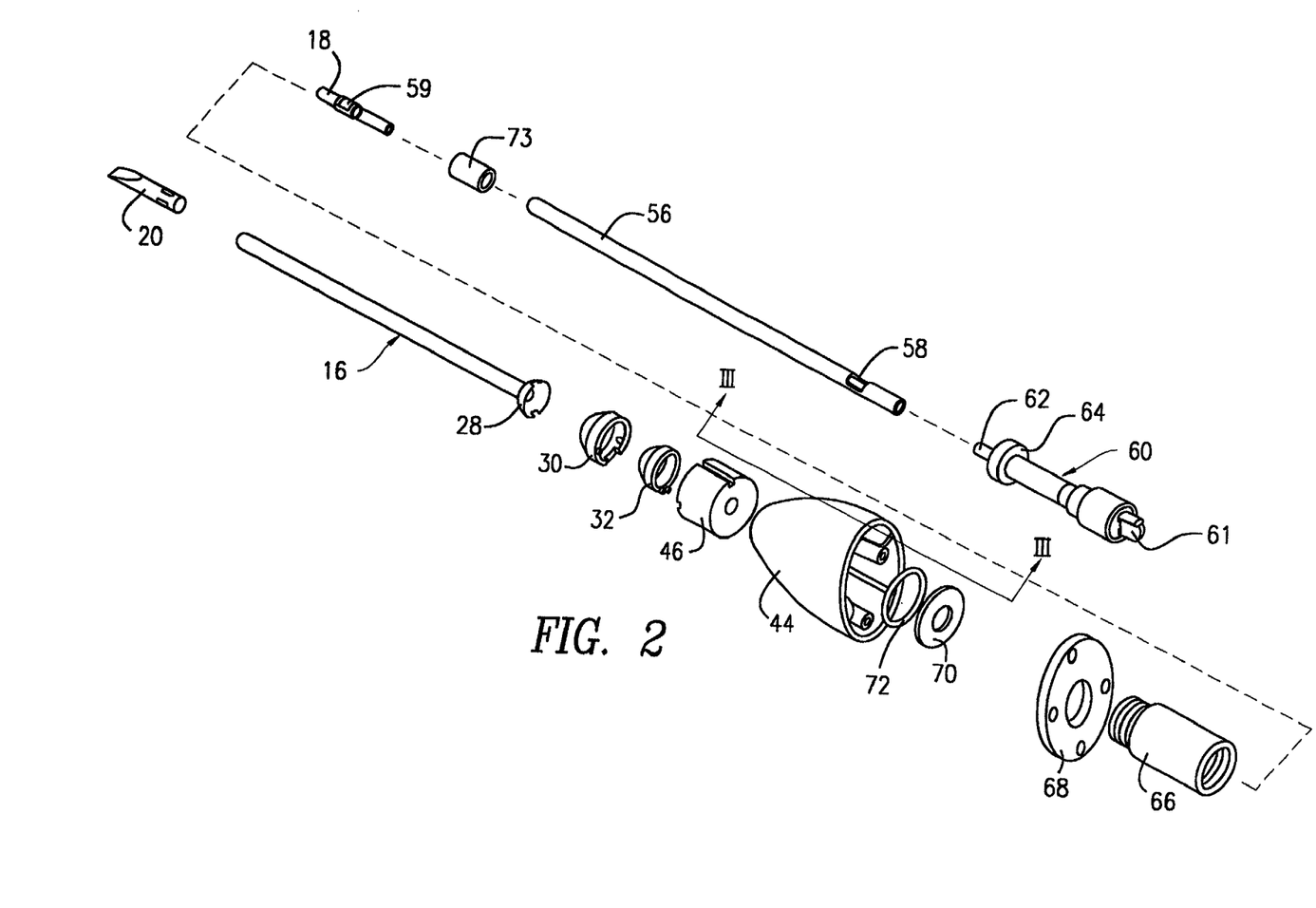
FIG. 2 is an exploded perspective view of the front tool assembly of the device of FIG. 1.

As shown in FIG. 2, the burr 18 is attached to a hollow burr shaft 56 having a fluid outlet 58 near the proximal end thereof. The burr 18 has a fluid inlet 59 that communicates with the hollow burr shaft 56. The burr shaft 56 attaches to drive shaft 60 at shaft tip 62. A bearing 64, such as a roller, ball or plain bearing is disposed on the drive shaft 60 to rotatably support the drive shaft 60 when the drive shaft 60 is inserted into barrel 66. Barrel 66 is threadedly or otherwise attached to flange 68, which is threadedly attached by screws or other fasteners to the housing 44. A bearing retainer 70 is utilized within the housing 44 in conjunction with an o-ring seal 72 for retaining the bearing 46 in position within the housing 44.

As shown in FIGS. 1 and 2, bearings 46 and 64 establish the orientation of the drive shaft 60 and burr shaft 56 relative to the housing 44. The orientation of the burr shaft 56 relative to the housing 44 establishes the orientation of the sheath tube 16 relative to the housing 44. More particularly, as shown in FIG. 3, when the burr shaft 56 is inserted through bearing 46 and sheath tube 16, 45 the burr shaft 56 supports the sheath tube 16 in alignment therewith. As noted above, the sheath tube 16 is otherwise free to move by an angular displacement $\alpha$ about the axis of the bearing 48, as well as by translations perpendicular to bearing 46 axis. This arrangement eliminates the transmission of force from the burr shaft 56 to the sheath tube 16, in that the sheath tube 16 rides freely upon the burr shaft 56 with the burr shaft 56 establishing the angular and translational orientation of the sheath tube 16. Since the sheath tube 16 does not structurally support the burr shaft 56, it can have a reduced wall thickness and/or may be formed from a less rigid material, such as a polymer, e.g., polycarbonate, urethane or silicone. A thinner walled sheath tube 16 allows the diameter of the burr shaft 56 to be increased, e.g., from 4.18 mm to 5.18 mm, thereby increasing the rigidity and strength of the burr shaft 56, such that unacceptable bending of the burr shaft 56 does not occur. A thin-walled sheath tube 16 also preserves the overall maximum outer diameter of the sheath tube 16 which is established by considerations of the dimensions of certain confined bodily spaces such as a knee joint. A spacer 73 may be provided on the burr shaft 56 proximate the burr 18 to aid in intermediating between the sheath tube 16 and the burr shaft 56.

As shown in FIG. 1, the bearings 46 and 64 are spaced one from another by a distance S and the burr shaft 56 and drive shaft 60 are rigidly connected to approximate a unitized shaft. Because the materials of the burr shaft 56 and drive shaft 60 are preferably very stiff, e.g., stainless steel, and the dimensions thereof sufficiently large, e.g., a burr shaft 56 with a diameter of 5.18 mm, flexure under the forces typically encountered during surgery is minimal. Given a stiff burr shaft 56/drive shaft 60 assembly, the only inadvertent displacement of the burr 18 that may occur would be attributable to bearing play. Since all bearings exhibit some play, the present invention spaces the bearings 46, 64 by a significant distance S. In this manner, any pivoting of the burr shaft 56/drive shaft 60 assembly at either bearing 46, 64 is arrested by the other bearing 64, 46, respectively. The greater the spacing S, the less angular pivoting is permitted at the bearings 46, 64. Because the bearings 46, 64 are located in the housing 44 and handle portion 12, the material composition, type and dimensions of the bearings 46, 64 is unrestricted relative to the very limited specifications required of a bearing positioned in a burr shaft sheath proximate a burr, as is common in known burr apparatus. As a result, advantages in burr 18 stability and increased feedback from burr 18 operation, i.e., to the surgeon's hand, can be achieved with the present invention.

FIGS. 6A–6C illustrate how the sheath tube 16 may be restrained from rotation relative to bearing 46 while permitting transverse displacements. FIG. 6A diagrammatically shows the concentric ball 32 and socket 30 elements viewed through a transparent bearing 46 with the tab 36, notch 40 and locator pins 38, 42 facing the viewer. The pin recesses 52, 54 as well as the key notch 48 are shown in dotted lines. In FIG. 6A, the ball 32 and socket 30 elements are coaxial with the bearing 46. Bearing 46 axis $A_1$ is depicted as a dot. Axis $A_2$ (small circle) is the axis of both the ball 32 and the socket 30 elements in all positions shown in FIGS. 6A–6C. FIG. 6A depicts the tab 36 residing centrally in notch 40, i.e., equidistant from notch walls 40a, 40b. The locator pins 38, 42 are positioned within the pin recesses 52, 54, respectively, with relative angular orientation β of about 90°. In FIG. 6B, the ball 32 and socket 30 elements are displaced transversely by a distance $D_{x1}$. This displacement results in a shifting of locator pin 42 to the left in pin recess 54. Ball element 32 rotates counterclockwise within socket element 30 under the influence of locator pin 38 being constrained by pin recess 52. The rotation of ball element 32 causes the tab 36 to approach notch wall 40b and angle β to increase beyond 90°.

FIG. 6C shows a transverse displacement in the positive X and positive Y directions, i.e., by $D_{x2}$ and $D_{y2}$. The consequence of this displacement is a shifting of the locator pins 38, 42 in pin recess 52, 54, the rotation of the tab 36 clockwise towards notch wall 40a and the decrease of angle β to be less than 90°.

Figure 7:
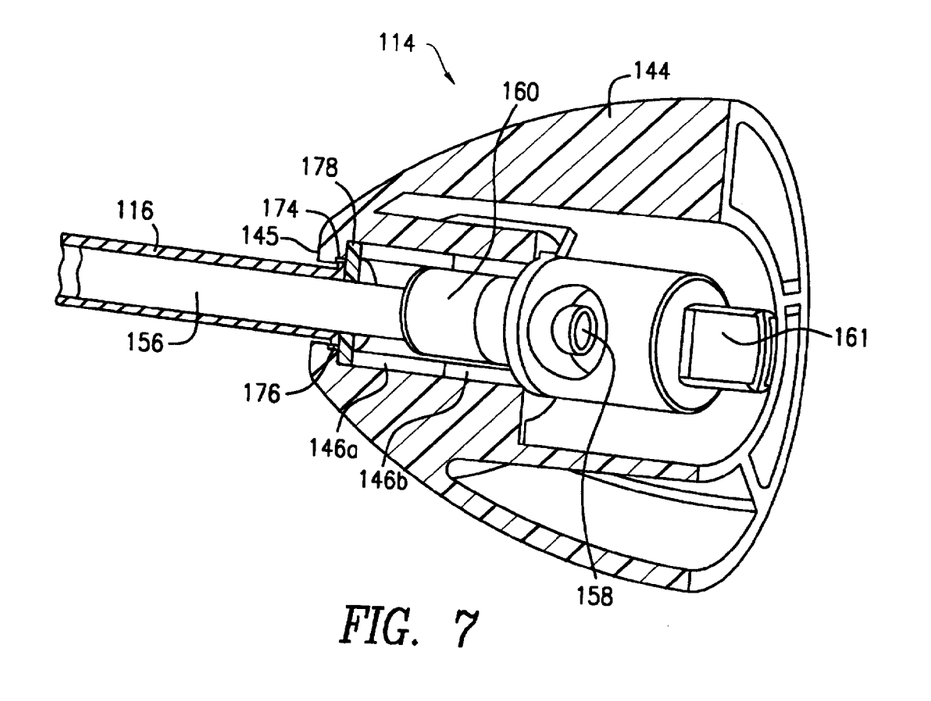
FIG. 7 is a cross-sectional view of a front tool assembly like FIG. 3, but of a second embodiment of the present invention.
Figure 8:
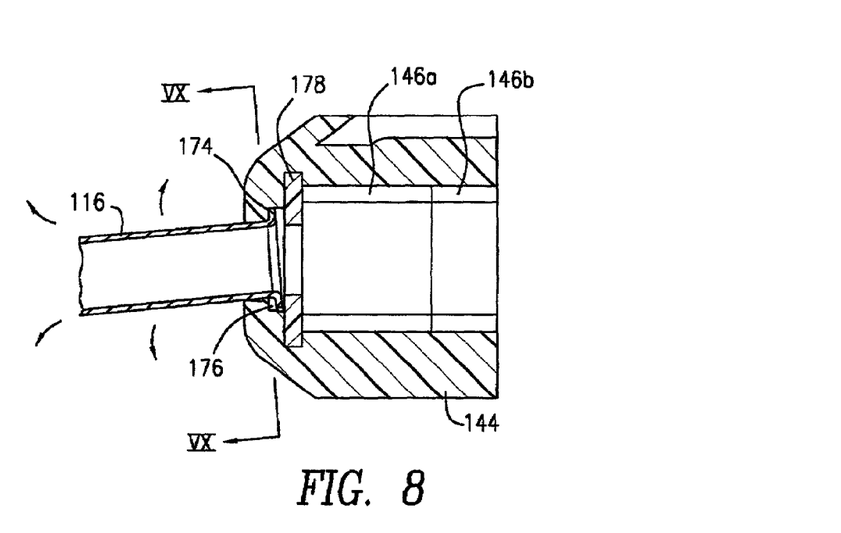
FIG. 8 is an enlarged fragment of the assembly of FIG. 7 with the burr shaft removed and the sheath tube hanging limp.

FIG. 7 shows an alternative embodiment of the front tool assembly 114. In the remainder of this specification, elements having similar function and structure as elements of preceding embodiments have been designated by reference numbers increased by multiples of 100 wherever possible. In FIG. 7, the burr shaft 156 establishes the orientation of the sheath tube 116 relative to the housing 144. As before, the sheath tube 116 has a degree of freedom of movement about the axis of the housing 144 when the burr shaft 156 is removed (transverse and angular pivot). FIGS. 7 and 8 illustrate that this functionality is accomplished by means of a flared end 174 provided on the sheath tube 116 which is received in a complementary oversized seat 176 provided in the distal end 145 of the housing 144. The space accommodating the flared end 174 is completed by a bushing 178 that delimits the space in the proximal direction. Because the space defined by the complementary oversized seat 176 and bushing 178 is larger than the flared end 174, the flared end is free to angularly articulate omni-directionally over a range of motion of displacement from the axis of the housing 144, as well as to move transversely, i.e., perpendicularly relative to the axis of bearing 146a.

Figure 9:
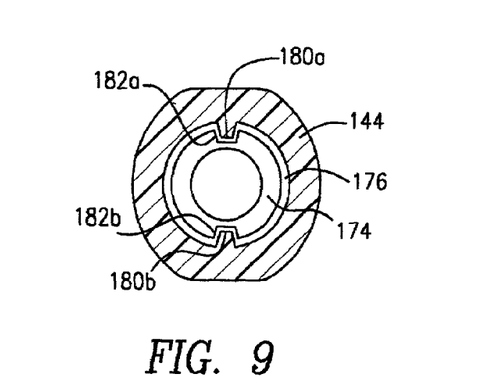
FIG. 9 is a cross-sectional view of the assembly of FIG. 8 taken along section line IX—IX and looking in the direction of the arrows.

FIG. 9 shows that the housing 144 in the area of the seat 176 has a pair of opposed anti-rotation keys 180a and 180b. The anti-rotation keys 180a, 180b are received in complementary anti-rotation notches 182a, 182b that are provided in the periphery of the flared end 174 of the sheath tube 116. As shown, the anti-rotation notches 182a, 182b are larger than the corresponding anti-rotation keys 180a, 180b to provide clearance to allow the sheath tube 116 to be translated and/or pivoted away from the axis of the housing 144 as shown in FIG. 7, but prevent axial rotation of the sheath tube 116 relative to the housing 144. Housing 144 supports a pair of plane bearings 146a, 146b to support the drive shaft 160 and burr shaft 156 in axial alignment with the housing 144. While two plane bearings 146a, 146b are shown, a single bearing could be utilized or another type of bearing, such as a ball bearing could be used. The fluid outlet 158 is disposed at the proximal end of the burr shaft 156 rather than on the side, like outlet 58 as shown in FIG. 2. Drive shaft 160 has a tab 161 extending therefrom that is intended to be received within a suitable bit/slot extending from the handle for transmitting motion from the actuator mechanism in the handle 12 to the drive shaft 160.

Figure 10:
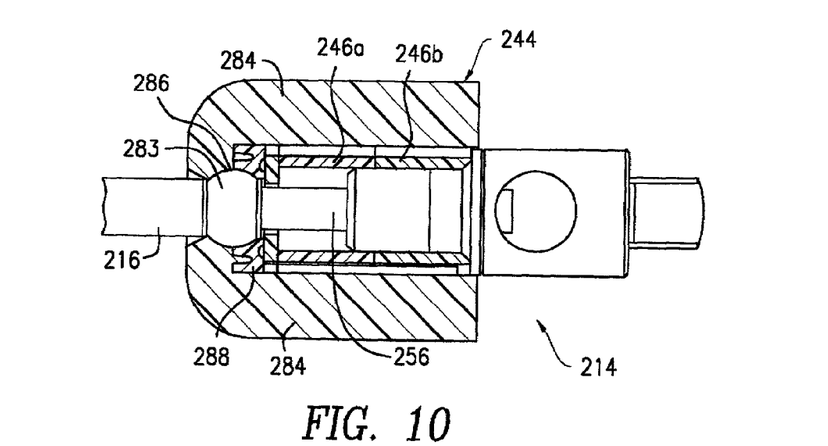
FIG. 10 is a cross-sectional view of a front tool assembly like FIG. 3, but of a third embodiment of the present invention.
Figure 11:
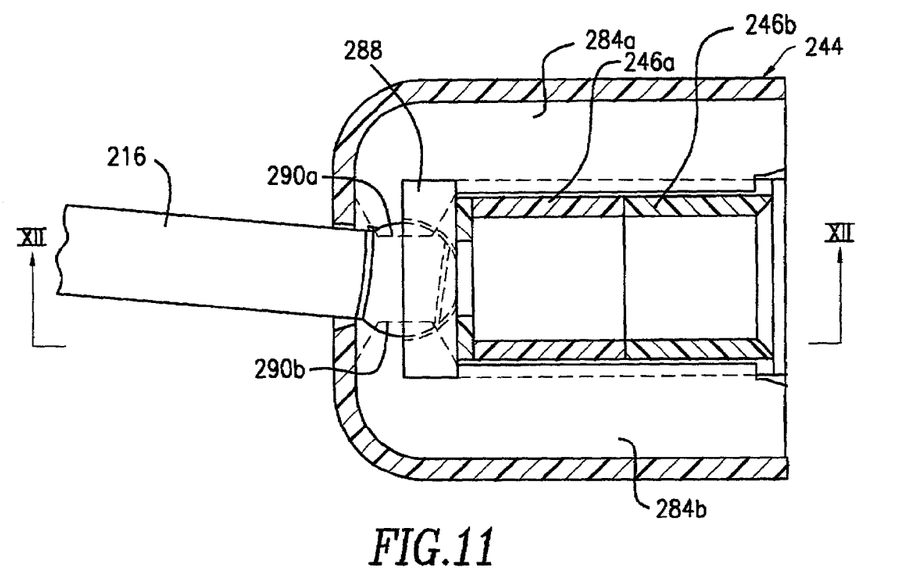
FIG. 11 is an enlarged cross-sectional view of the assembly of FIG. 10 with the burr shaft removed and the sheath tube displaced from concentricity with the assembly.
Figure 12:
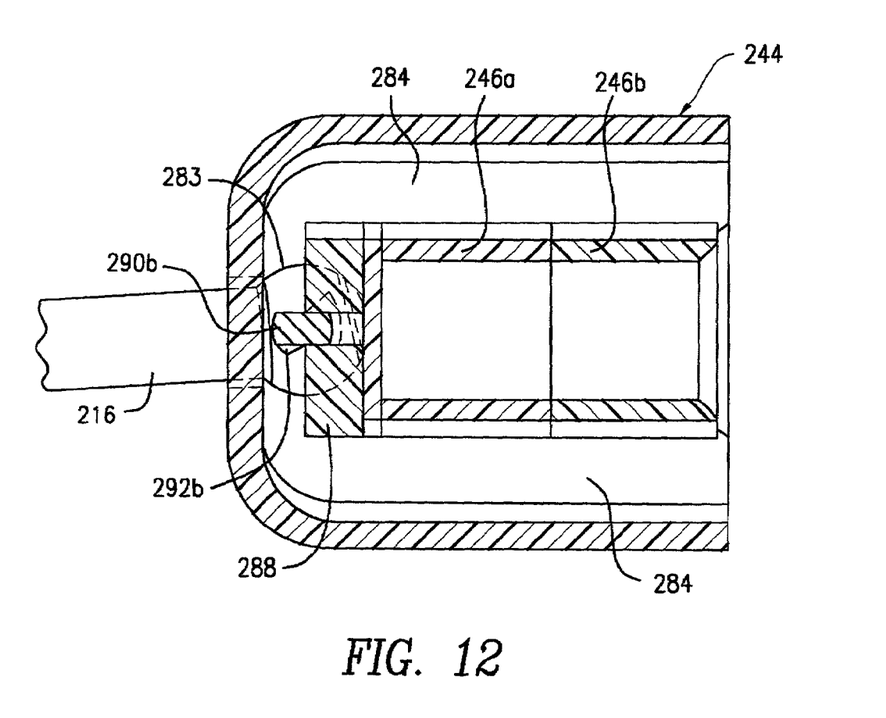
FIG. 12 is a cross-sectional view of the assembly of FIG. 11, taken along line XII—XII and looking in the direction of the arrows.

FIGS. 10–12 show an alternative embodiment of the present invention wherein the sheath tube 216 has a generally spherical member 283 disposed at the proximal end thereof. The housing 244 has a plurality of inwardly directed ribs 284 which define a ball socket 286 at the distal end thereof that approximates a hemisphere. A removable socket cap 288 is keyed to at least one of the ribs 286 and captures the ball 283 of the sheath tube 216 within the socket 286, permitting the sheath tube 216 to articulate relative to the housing 244. To prevent rotation of the sheath tube 216, a pair of the ribs, i.e., 284a, 284b are specifically configured to be anti-rotation ribs. The ends 290a, 290b of ribs 284a, 284b are each received in a bow-tie shaped anti-rotation notch 292a, 292b on the spherical member 283 of the sheath tube 216. As shown in FIG. 11, the relative sizing of the ends 290a, 290b of the anti-rotation ribs and the bow-tie shape anti-rotation notches 292a, 292b permit the spherical member 283 to be articulated omni-directionally over a range of motion, namely displaced from the axial orientation by angle α. More particularly, the bow-tie shape anti-rotation notches 292a (not visible), 292b are longer then the ends 290a, 290b, permitting the ball to be pivoted along an axis parallel to the anti-rotation ribs. The bow-tie shape of anti-rotation notches 292a, 292b allow the pivoting of the ball along an axis perpendicular to the anti-rotation ribs 286a, 286b. If desired, a selected amount of clearance can be provided between mating elements, e.g., ball 283 and socket 286 to permit transverse motion of the sheath tube 216.

Figure 13:
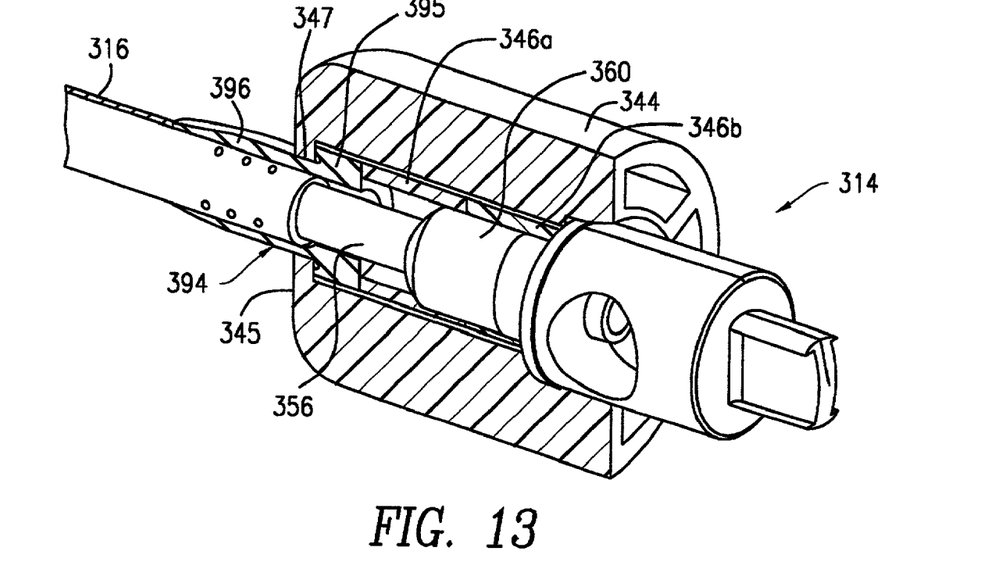
FIG. 13 is a cross-sectional view of a front tool assembly like FIG. 3, but of a fourth embodiment of the present invention.

FIG. 13 shows an embodiment wherein the sheath tube 316 is glued, plastic welded or otherwise adhered to a flexible grommet 394, e.g., fabricated from an elastomer which extends through the housing 344. More specifically, the grommet 394 has a flange 395 that prevents the grommet 394 from passing through opening 347 in the distal end 345 of the housing 344. A ferrule 396 extends through the opening 347 and increases the contact area between the grommet 394 and the sheath tube 316. Since the rubber grommet 394 is flexible, the sheath tube 316 is displaceable omni-directionally and, if desired, transversely from the axis of the housing 344. One or more bearings 346a, 346b support the drive shaft 360 and bearing 346a abuts the flange 395. The grommet 394 may be glued, plastic welded or otherwise attached to the housing 344 to prevent rotation. Alternatively, the grommet 394 may be provided with a notch or other surface features that mate with corresponding surface features of the housing 344 or may be press-fit into the housing 344 to exhibit a resistance to rotation due to friction.

Figure 14:
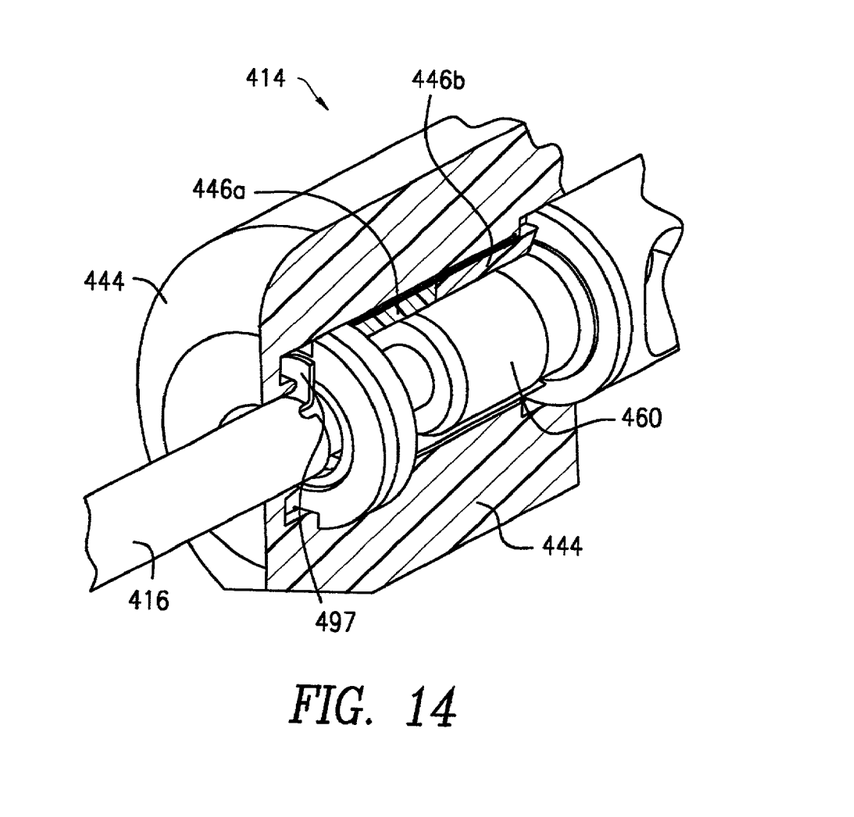
FIG. 14 is a cross-sectional view of a front tool assembly like FIG. 3, but of a fifth embodiment of the present invention.
Figure 15:
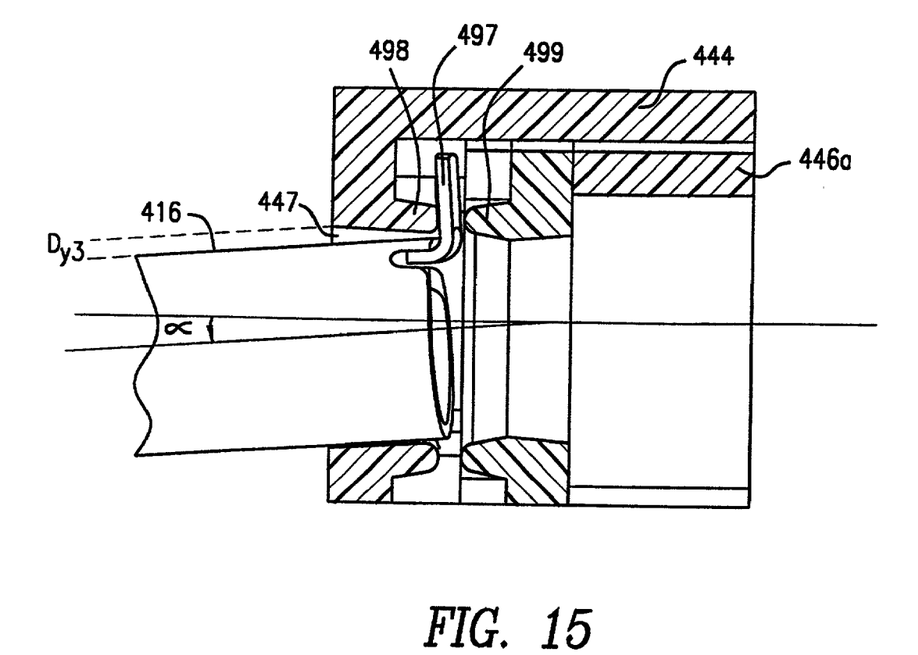
FIGS. 15 and 16 are enlarged cross-sectional views of the front tool assembly of FIG. 14, with FIG. 15 having the burr shaft removed and FIG. 16 showing the burr shaft in place.
Figure 16:
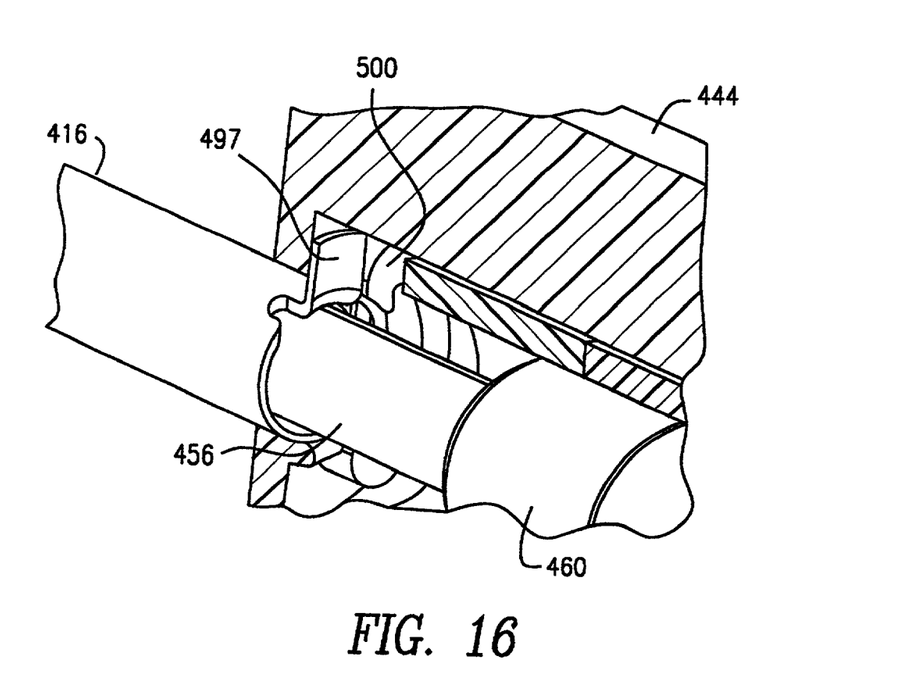
Figure 17:
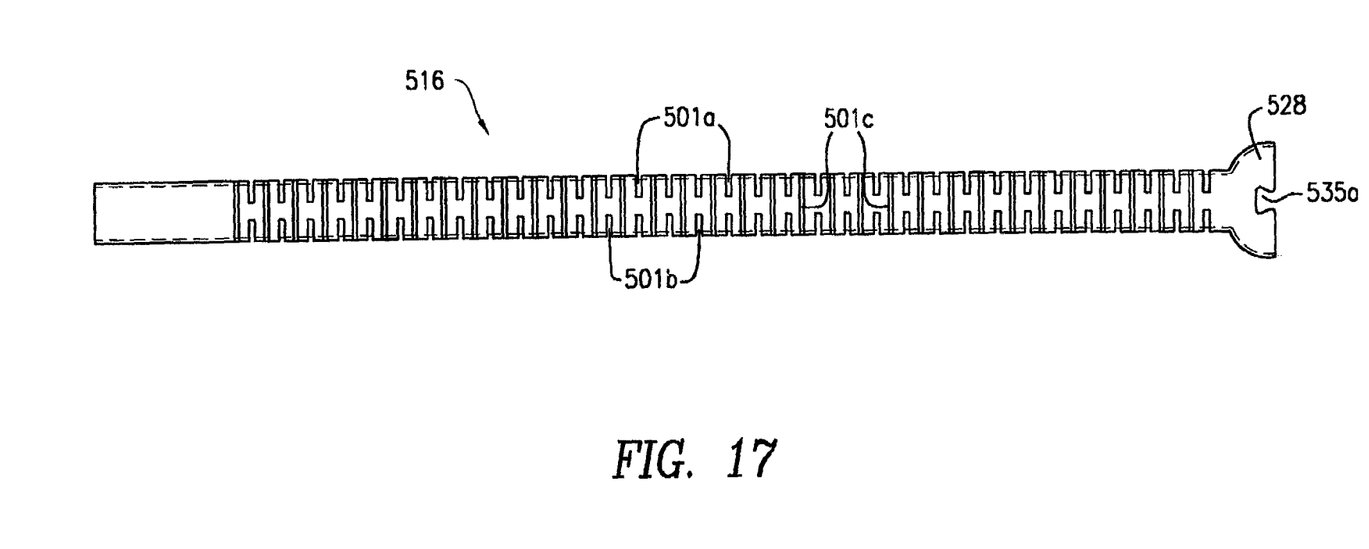
FIG. 17 is a sheath tube in accordance with an alternative embodiment of the present invention.

FIGS. 14–16 depict an alternative embodiment of the front tool assembly 414 of the present invention, wherein the sheath tube 416 has an upwardly extending tang 497 disposed approximately at right angles to the axis of the sheath tube 416. The tang 497 is loosely constrained by an integral motion limiter 498 extending from the housing 444 proximate opening 447 and by a removable motion limiter bushing 499 that is inserted into the housing 444 after the sheath tube 416 has been inserted therein. As shown in FIG. 15, the housing 444 also incorporates a pair of cardioid anti-rotation members 500 between which the tang 497 is positioned loosely. As before, the sheath tube 416 is loosely retained within the housing 444 such that it articulates omni-directionally by displacement angle α relative to the axis of the housing 444 and/or translates by displacement $D_{y3}$ and therefore does not provide a structural support for retaining the burr shaft 456 in alignment with the housing 444. Rather, the sheath tube 416 is retained in alignment relative to the burr shaft 456.

FIG. 16 shows a sheath tube 516 for use in the embodiment of the present invention shown in FIGS. 2–5. The sheath tube 516 has been altered by providing a plurality of opposing slots 501a, 501b, 501c, 501d (rear-not visible in this view). The slots 501a, 501b, 501c, 501d render the sheath tube 516 more flexible, such that any displacement of the burr shaft 56 (not shown) can be accommodated by a corresponding dynamic bending of the sheath tube 516. As can be appreciated, other slot arrangements, such as a spiral slot, could be utilized while preserving the same functionality of the sheath tube 516. In addition, because the sheath tube, for example 16 or 516 does not provide a structural supporting function relative to the burr shaft 56, it can be formed from a flexible material, such as a polymer. In the case of a highly flexible sheath tube, the proximal end may be rigidly fixed to the housing 44.

It should be understood that the embodiments described herein are merely exemplary and that a person skilled in the art may make many variations and modifications without departing from the spirit and scope of the invention as defined in the appended claims. For example, FIGS. 1 and 2 illustrate a distal bearing 46 disposed in the housing 44 and a proximal bearing 64 retained in a barrel 66 coupled to the housing 44 via flange 68. An alternative method for holding bearing 64 would be to retain it in the handle portion 12 and slideably insert drive shaft 60 therethrough to couple to the driving mechanism. In that case, the drive shaft 60 would be configured to slide into the bearing 64 in a distal direction, viz., by having a diameter which may be received in the bearing 64.

It should be understood that the embodiments described herein are merely exemplary and that a person skilled in the art may make many variations and modifications without departing from the spirit and scope of the invention as defined in the appended claims. Accordingly, all such variations and modifications are intended to be included within the scope of the invention as defined in the appended claims.

We claim:

1. A surgical tool for removing material from a surface, comprising:
   a front tool assembly coupled to a handle, the front tool assembly comprising a housing and a rotatable burr shaft extending therefrom with a burr attached at one end of the burr shaft and a rotary drive apparatus coupled to the other end for selectively rotating the burr shaft as controlled by a user; and,
   a sheath tube disposed substantially coaxially over the burr shaft and attached at a first end to the front tool assembly housing and having an opening proximate a second end thereof through which said burr contacts the surface for removing material, said sheath tube being attached to said front tool assembly housing at an articulation, said articulation enabling said sheath tube to be displaced from axial alignment with said front tool assembly housing.

2. The surgical tool of claim 1, wherein said articulation comprises a ball joint.

3. The surgical tool of claim 2, wherein said first end of said sheath tube is in the form of a portion of a sphere, wherein said ball joint further comprises a male ball that is matingly received within said portion of a sphere, and a female socket having an interior spheric surface approximating the exterior shape of said first end of said sheath tube, wherein said first end of said sheath tube is slideably captured between said male ball and said female socket.

4. The surgical tool of claim 3, wherein one of said male ball and said female socket shell has an anti-rotation rib extending from a surface thereof and said first end of said sheath tube has an anti-rotation notch receiving said anti-rotation rib therein to prevent said sheath tube from rotating relative to said housing.

5. The surgical tool of claim 4, wherein said male ball and said female socket are coupled by a tab and mating notch to limit relative rotation.

6. The surgical tool of claim 2, wherein a clearance is present between said ball joint and said front tool assembly housing, said clearance permitting said sheath tube to articulate transversely relative to said tool assembly housing.

7. The surgical tool of claim 1, wherein said first end of said sheath tube additionally comprises a peripheral flange, said housing having a seat with a shape generally complementary to said peripheral flange to loosely receive said peripheral flange therein and a bushing positioned proximate a proximal edge of said seat and said flange, said bushing retaining said sheath tube in association with said housing and preventing movement of said sheath tube in a proximal direction, said seat having a rib extending radially inwardly and said flange having a radial notch, said notch receiving said rib therein to prevent said sheath tube from rotating relative to said housing.

8. The surgical tool of claim 7, further comprising a bearing for rotatably supporting the burr shaft distal to the burr, said bearing inserting into said housing and having a slot extending along an outer peripheral surface thereof in an axial direction, said housing having a key extending inwardly, said slot receiving said key to retain said bearing in a fixed orientation relative to said housing.

9. The surgical tool of claim 1, wherein said first end of said sheath tube has an approximately spheric shape and said housing has a generally spherically shaped socket for receiving said first end of said sheath tube.

10. The surgical tool of claim 9, wherein said socket has a first portion integral with said housing and a second portion in the form of a removable seat, said first end of said sheath tube captured between said first portion and said second portion.

11. The surgical tool of claim 10, wherein said socket first portion is defined by a plurality of inwardly directed ribs the interior surfaces of which are disposed along contours of a spheric shape approximating that of said first end, one of said ribs having a tip extending inwardly to an extent that said tip extends below the surface of said first end, said first end being provided with a recess for receiving said tip therein, said tip preventing the rotation of said sheath tube relative to said housing, said recess having a greater cross-sectional area than said tip and having a bow-tie shape to permit said sheath tube to be articulated relative to said housing.

12. The surgical tool of claim 11, further comprising a bushing abutting said seat, said bushing retaining said removable seat abutting said first portion to prevent movement of said sheath in a proximal direction and a bearing for rotatably supporting the burr shaft distal to the burr, said bearing inserting into said housing and having a slot extending along an outer peripheral surface thereof in an axial direction, said housing having a key extending inwardly, said slot receiving said key to retain said bearing in a fixed orientation relative to said housing.

13. The surgical tool of claim 1, wherein said first end of said sheath tube has an elastomeric flange affixed thereto and said housing has a complementary seat therein for receiving said flange, said flange having a flexibility allowing said sheath tube to articulate relative to said housing.

14. The surgical tool of claim 13, wherein said flange has a ferrule extending therefrom in a direction perpendicular to said flange, said ferrule attaching to said sheath tube and further comprising a bearing for rotatably supporting the proximal end of the burr shaft, said bearing inserting into said housing and having a slot extending along an outer peripheral surface thereof in an axial direction, said housing having a key extending inwardly, said slot receiving said key to retain said bearing in a fixed orientation relative to said housing, said bearing abutting against said flange, capturing said flange between said housing and said bearing to prevent rotation of said flange relative to said housing.

15. The surgical tool of claim 1, wherein said first end of said sheath tube has a tang extending at right angles thereto and said housing has a complementary seat therein for loosely receiving said tang, allowing said sheath tube to articulate relative to said housing and further comprising a bushing insertable in said housing to abut said tang, said bushing retaining said sheath tube in association with said housing and limiting movement of said sheath tube in a proximal direction.

16. The surgical tool of claim 15, wherein said seat has a pair of abutment surfaces disposed on either side of said tang, said abutment surfaces preventing said sheath tube from rotating relative to said housing, said seat having a tang engagement bumper extending from said housing in a proximal direction and contacting said tang at a point intermediate between said sheath tube and a free end of said tang, said tang pivoting about said contact point with said tang engagement bumper when articulated, said bushing having an annular tang engagement bumper opposing said tang engagement bumper extending from said housing and capturing said tang there between.

17. The surgical tool of claim 16, wherein said housing has a support lip disposed opposite said tang engagement bumper, said support lip extending generally parallel to said tang engagement bumper in a proximal direction for supporting said first end of said sheath tube.

18. The surgical tool of claim 1, wherein said articulation enables said sheath tube to be translated perpendicularly and angularly displaced from axial alignment with said front tool assembly housing.

19. A surgical tool for removing material from a surface, comprising:
   a front tool assembly coupled to a handle, the front tool assembly comprising a housing and a rotatable burr shaft extending therefrom with a burr attached at one end of the burr shaft and a rotary drive apparatus coupled to the other end for selectively rotating the burr shaft as controlled by a user;
   a sheath tube disposed substantially coaxially over the burr shaft and attached at a first end to the front tool assembly housing and having an opening proximate a second end thereof through which said burr contacts the surface for removing material, said sheath tube being attached to said front tool assembly housing at an articulation, said articulation enabling said sheath tube to be displaced from axial alignment with said front tool assembly housing; and
   a bearing for rotatably supporting the burr shaft distal to the burr, said bearing inserting into said housing substantially coaxially with said ball joint, capturing said ball joint between a distal tip of said housing and said bearing, said bearing having a first slot extending along an outer peripheral surface thereof in an axial direction and said housing having a key extending inwardly, said slot receiving said key to retain said bearing in a fixed orientation relative to said housing, said bearing having an end surface facing said tip of said housing, said end surface having second and third slots therein, said male ball and said female socket each having an anti-rotation pin extending in a proximal direction therefrom and received in said second and third slots respectively to limit rotation of said male ball and said female socket relative to said bearing.

20. A surgical tool for removing material from a surface, comprising:
   a front tool assembly coupled to a handle, the front tool assembly comprising a housing and a rotatable burr shaft extending therefrom with a burr attached at one end of the burr shaft and a rotary drive apparatus coupled to the other end for selectively rotating the burr shaft as controlled by a user;
   a sheath tube disposed substantially coaxially over the burr shaft and attached at a first end to the front tool assembly housing and having an opening proximate a second end thereof through which said burr contacts the surface for removing material, said sheath tube being attached to said front tool assembly housing at an articulation, said articulation enabling said sheath tube to be displaced from axial alignment with said front tool assembly housing; and a first bearing supporting said burr shaft and disposed between said articulation and the rotary drive apparatus, a second bearing supporting said burr shaft and disposed between said first bearing and the rotary drive apparatus, said first bearing and said second bearing are spaced one from another.

* * * * *